(12) United States Patent
Di Giovanni et al.

(10) Patent No.: US 6,315,173 B1
(45) Date of Patent: *Nov. 13, 2001

(54) VALVE FOR AEROSOL CONTAINER

(75) Inventors: Patrick Di Giovanni, Le Vaudrueil (FR); Cheryl Vanessa Rogerson, Essex (GB)

(73) Assignee: SmithKline Beecham Corporation, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/709,084

(22) Filed: Nov. 10, 2000

Related U.S. Application Data (6362) Continuation of application No. 09/331,801, filed as application No. PCT/EP97/07224 on Dec. 23, 1997, now Pat. No. 6,170,717.

(30) Foreign Application Priority Data

Dec. 27, 1996 (GB) .................................................. 9626960

(51) Int. Cl.[7] .................................................. B65D 83/54
(52) U.S. Cl. ..................................... 222/402.2; 222/402.1
(58) Field of Search ............................... 222/328, 402.19, 222/402.2, 402.24, 402.1, 547, 564

(56) References Cited

U.S. PATENT DOCUMENTS

| | | | |
|---|---|---|---|
| 4,867,352 | * 9/1989 | Meshberg | 222/402.2 |
| 4,944,433 | 7/1990 | Knecht et al. | |
| 5,037,012 | 8/1991 | Langford. | |
| 5,632,421 | * 5/1997 | Colombo | 222/402.2 |
| 5,697,532 | 12/1997 | Wilde et al. | |
| 5,904,274 | 5/1999 | Warby et al. | |
| 6,170,717 | * 1/2001 | Di Giovanni et al. | 222/402.2 |

* cited by examiner

*Primary Examiner*—Kenneth Bomberg
(74) *Attorney, Agent, or Firm*—Christopher P. Rogers

(57) ABSTRACT

Valve for an aerosol container for dispensing a suspension of a substance in a liquid propellant contained therein The valve comprises a valve body (1) having at least one orifice (16) to allow a quantity of the suspension to pass from the container into the valve. The valve further comprises a ring (18) disposed around the valve body (1), the ring being positioned below the at least one orifice to reduce the volume of suspension that can be accommodated within the container below the at least one orifice when the container is orientated with the valve at the bottom, the ring having at least one portion of reduced axial thickness to provide a trough (19) around the valve body below the at least one orifice.

39 Claims, 3 Drawing Sheets

VALVE FOR AEROSOL CONTAINER

Figure 1:
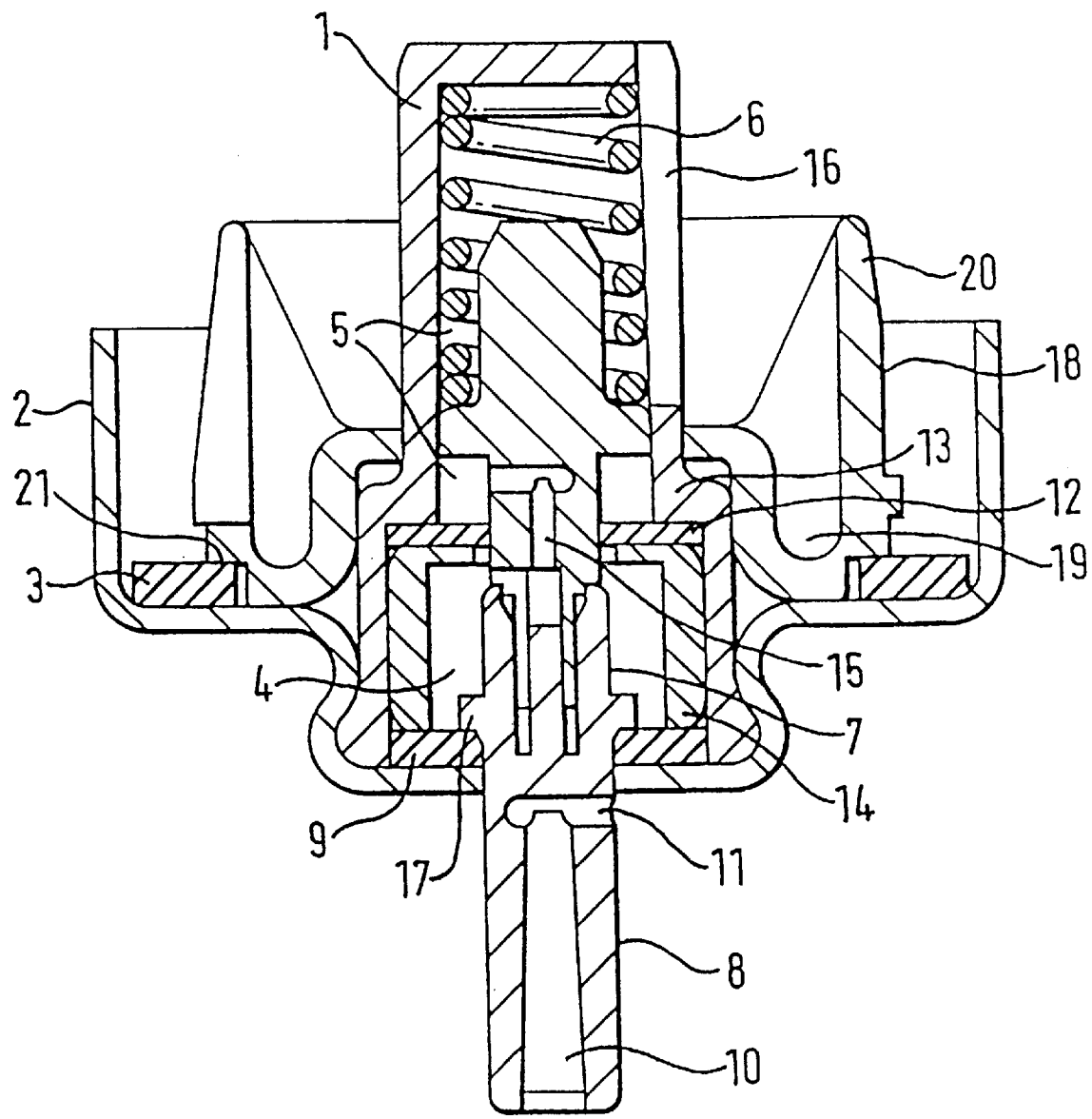

This application is a continuation of U.S. patent application Ser. No. 09/331,801 filed Sep. 13, 1999, now U.S. Pat. No. 6,170,717, which is a 371 of PCT/EP97/07224 filed Dec. 23, 1997.

This invention relates to a valve for an aerosol container with the aid of which a quantity of the contents thereof can be dispensed. The invention has particular application to the dispensing of metered doses of medicaments, though it is applicable to the dispensing of aerosols generally.

In dispensing a solid in aerosol form it is common to use what is known as a suspension aerosol. This involves the use of a liquid propellant in which a solid to be dispensed is suspended. There is inevitably some difference, however slight, between the respective specific gravities of the propellant and the solid to be dispensed, which means that, with the passage of time and in the absence of other overriding interactions, the two components tend to separate in the container, with a lighter component going to the top or a heavier component going to the bottom over time.

In some pharmaceutical aerosols the particles of medicament are more dense than the propellant and hence the particles tend to sediment out to the bottom of the container. This phenomenon may be accentuated by the additional structuring of the medicament presentation necessary to enhance its physical stability, for example by controlled flocculation thereof. Controlled flocculation of the suspension may increase the effective particle size in dispersion from less than 10 $\mu$m to greater than 100 $\mu$m. A squared dependency on particle radius will directly increase the sedimentation rate in such circumstances.

Users of suspension aerosols are always instructed before use to shake the container well. However, even a short interval between the conclusion of the shaking and the act of dispensing a charge from the aerosol is sufficient to allow some sedimentation to occur. This represents a particular problem where the suspended material is a medicament, since it can result in the patient receiving a dose which, although of the correct volume, contains either too little or too much of the medicament.

This problem has been found to be particularly acute in the development of CFC-free aerosol formulations using propellant 1,1,1,2-tetrafluoroethane, also known as HFA134a, which is less dense than conventional CFC containing propellants. With some aerosol drug formulations using this propellant, when the container is orientated with the valve at the bottom, the drug particles rapidly sediment onto and around the valve, and with vibration caused by, for example, transportation, find their way into the valve body. The trapped drug is then not fully dispensed, even on shaking due to the confinement of the valve body, and on discharge of valve actuation the trapped drug enters the metering chamber which leads to a high drug content in the dose delivered by the following actuation. This problem is especially pronounced where the drug is fluticasone propionate.

UK Patent No. 2195986 describes an aerosol valve wherein the pick-up point, i.e. the point at which liquid passes from the interior of the container into the sampling chamber of the valve, is at a location which, when the container is orientated with the valve at the bottom, is spaced an appreciable vertical distance from the nearest substantially horizontal surface. Whilst this valve ensures that the liquid entering the metering chamber following a dispensing operation comes from above the nearest region where sedimented drug particles might gather, any sedimenting drug particles that might be drawn into the sampling chamber together with any drug particles that sediment out of the suspension within the sampling chamber tend to be trapped and are not dispensed on shaking. Furthermore, by deliberately placing the pick-up point appreciably higher than the lowest point in the container, a significant quantity of the contents of the container cannot be dispensed, which results in considerable wastage.

It is an object to provide a valve which alleviates these problems.

According to the present invention there is provided a valve for an aerosol container for dispensing a suspension of a substance in a liquid propellant contained herein, the valve comprising a valve body having at least one orifice to allow a quantity of the suspension to pass from the container into the valve, characterised in that the valve further comprises a ring disposed around the valve body, the ring being positioned below the at least one orifice to reduce the volume of suspension that can be accommodated within the container below the at least one orifice when the container is orientated with the valve at the bottom, the ring having at least one portion of reduced axial thickness to provide a trough around the valve body below the at least one orifice.

By providing a ring below the at least one orifice to reduce the volume of suspension that can be accommodated within the container below the orifice(s) when the container is orientated with the valve at the bottom, it ensures that most of the contents of the container may be dispensed to reduce wastage, while the trough around the valve body below the orifice(s) provided by the at least one portion of reduced axial thickness serves to accommodate any drug particle sediment so ensuring that the suspension entering the sampling chamber comes from above the region where any sedimented drug particles might gather.

Preferably, the valve is a metering valve comprising a metering chamber, a sampling chamber, a transfer passage through which a quantity of suspension can pass from the sampling chamber to the metering chamber, and a valve stem having a dispensing passage through which a dose of suspension can be dispensed from the metering chamber, the valve stem being slideably moveable within the valve body such that in a first position the dispensing passage is isolated from the metering chamber and the metering chamber is in communication with the sampling chamber via the transfer passage, and in a second position the dispensing passage is in communication with the metering chamber and the transfer passage is isolated from the metering chamber the valve body having a plurality of orifices to allow a quantity of the suspension to pass from the container into the sampling chamber.

By providing a valve body having a plurality of orifices to allow the suspension to pass from the container into the sampling chamber, the suspension may flow freely through the sampling chamber so allowing the suspension contained within the sampling chamber and the container to mix when the container is shaken and so disperse any drug particle sediment within the sampling chamber.

Suitably the orifices are slots extending in a substantially axial direction. Preferably the slots extend substantially-the entire axial length of the sampling chamber.

By providing slots the length of the sampling chamber the suspension may flow freely through the entire sampling chamber, so allowing maximum dispersion of drug particle sediment within the sampling chamber.

Preferably there are more than two slots.

Suitably the ring further comprises a seat to locate a gasket between the container and valve for sealing the container.

By providing a seat on the ring to locate the gasket, the gasket is reduced in size, and the area of gasket exposed to the contents of the container is also reduced.

Suitably the ring further comprises a plurality of vanes separated by slots at its periphery and extending substantially upwardly when the container is orientated with the valve at the bottom.

By providing vanes separated by slots at the periphery of the ring the suspension is made to flow around the vanes and through the slots when the container is shaken, and the resulting swirling motion of the suspension helps to disperse any drug particle sediment on and around the ring.

Suitably the substance to be dispersed is a medicament suspended in liquefied HFA134a. Preferably the medicament is fluticasone propionate.

The invention will now be described further with reference to the accompanying drawings in which:

FIG. 1 in a section through a metering valve according to a first embodiment of the invention;

FIG. 2 is a section through a metering valve according to a second embodiment of the invention; and FIG. 3 is a partly cut away perspective view of a ring for use with a valve according to the invention.

The valve according to a first embodiment of the invention as shown in FIG. 1 comprises a valve body 1 sealed in a ferrule 2 by means of crimping, the ferrule itself being set on the neck of a container (not shown) with the interposition of a gasket 3 in a well-known manner. The container is filled with a suspension of a medicament in liquid propellant HFA134a. Medicaments suitable for this purpose are, for example for the treatment of respiratory disorders such as asthma, bronchitis, chronic obstructive pulmonary diseases and chest infections. Additional medicaments may be selected from any other suitable drug useful in inhalation therapy and which may be presented as a suspension. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or neodocromil; antiinfectives e.g. cephalosporins, penicillins, streptomycin, sulphonamides, tetracyclines and pentamidine.; antihistamines, e.g. methapyrilene; anti-inflammatories e.g. fluticasone propionate, beclomethasone dipropionate, flunisolide, budesonide, or triamcinolone acetonide; antitussives, e.g. noscapine; bronchodilators, e.g. salmeterol, salbutamol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol orciprenaline, or (–)-4-amino-3,5-dichloro-α-[[[6-[2-(2-pyddinyl)ethoxy]-hexyl] amino]methyl] benzenemethanol; diuretics, e.g. amiloride; anticholinergics e.g. ipratropium, atropine or oxitropium; hormones, e,g, cortisone, hydrocortisone or prednisolone; xanthines e.g. aminophylline, choline theophyllinate, lysine theophyllinate or theophylline and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament. Preferred medicaments are salbutamol, salbutamol sulphate, salmeterol, salmeterol xinafoate, fluticasone propionate, beclomethasone dipropionate and terbutaline sulphate. It is to be understood that the suspension of medicament may consist purely of one or more active ingredients.

The valve body 1 is formed at its lower part with a metering chamber 4,and its upper part with a sampling chamber 5 which also acts as a housing for a return spring 6.The words "upper" and "lower" are used for the container when it is in a use orientation with the neck of the container and valve at the lower end of the container which corresponds to the orientation of the valve as shown in FIG. 1. Inside the valve body 1 is disposed a valve stem 7, a part 8 of which extends outside the valve through lower stem seal 9 and ferrule 2.The stem part 8 is formed within an inner axial or longitudinal canal 10 opening at the outer end of the stem and in communication with a radial passage 11.

The upper portion of stem 7 has a diameter such that it can pass slideably through an opening in an upper stem seal 12 and will engage the periphery of that opening sufficiently to provide a seal. Upper stem seal 12 is held in position against a step 13 formed in the valve body I between the lower and upper parts by a sleeve 14 which defines the metering chamber 4 between lower stem seal 9 and upper stem seal 12.The valve stem 7 has a passage 15 which, when the stem is in the inoperative positive shown, provides a communication between the metering chamber 4 and sampling chamber 5, which itself communicates with the interior of the container via orifices 16 formed in the side of the valve body 1. The orifices 16 comprise three slots arranged equi-angularly around the valve body 1 and extending in an axial direction with respect thereto, each slot having a width of approximately 1 mm and a length slightly less than the length of the sampling chamber 5 so that the suspension within the container can flow freely through the entire sampling chamber 5.

Valve stem 7 is biased downwardly to the inoperative position by return spring 6 and is provided with a shoulder 17 which abuts against lower stem seal 9.In the inoperative position as shown in FIG. 1 shoulder 17 abuts against lower stem seal 9 and radial passage 11 opens below lower stem seal 9 so that the metering chamber 4 is isolated from canal 10 and suspension inside cannot escape.

A ring 18 is disposed around the valve body below the slots, and is formed with a number of portions of reduced axial thickness giving a "U" shaped cross section extending in a radial direction so as to form a number of troughs 19 around the valve body. As seen in FIGS. 1 and 3,the ring is formed as a separate component made of nylon or any other suitable material, and has an inner annular contacting rim of a diameter suitable to provide a friction fit over the upper part of valve body 1, the ring seating against step 13 below the slots 16. However, the ring 18 may alternatively be formed as an integrally moulded part of valve body 1.

The outer wall of the ring is extended in an axial direction and is formed with a number of equi-angularly spaced slots to create vanes 20 which extend upwards from the lower part of the ring, as best seen in FIG. 3. In the ring depicted in FIG. 3, there are six slots and six vanes, though not all are shown in view of the cut away portion. However, it will be clear that more or fewer slots and vanes could be used. The lower part of the ring is further provided with a seat 21 for gasket 3 which helps to locate the gasket in the correct position during assembly and also allows the inner diameter of the gasket to be increased, thereby reducing the mass of the gasket and the area of gasket exposed to the material within the container. This can offer a significant advantage where there are problems with impurities being leached out of the gasket into the material contained.

To use the device, the container is shaken to homogenise the suspension within the container. As the container is shaken, the suspension in the container flows freely through the slots 16 in the sampling chamber 5, so ensuring that the suspension in the sampling chamber is thoroughly mixed with the suspension in the container. Not only does this ensure homogeneity of suspension within the container and sampling chamber, but the flow of suspension also serves to disperse any drug particle sediment that may have precipitated out of suspension within the sampling chamber 5. Shaking of the container also causes the suspension to flow around the vanes 20 and the resulting turbulence and swirling motion of the suspension helps to disperse any drug particle sediment on and around the ring.

The user then depresses the valve stem 7 against the force of the spring 6. When the valve stem is depressed, both ends of the passage 15 come to lie on the side of upper stem seal 12 remote from the metering chamber 4. Thus a dose is metered within the metering chamber. Continued depression of the valve stem will move the radial passage 11 into the metering chamber 4 while the upper stem seal 12 seals against the valve stem body. Thus, the metered dose can exit through the radial passage 11 and the outlet canal 10.

Releasing the valve stem causes it to return to the illustrated position under the force of the spring 6. The passage 15 then once again provides communication between the metering chamber 4 and the sampling chamber 5. Accordingly, at this stage liquid passes under pressure from the container through slots 16, through the passage 15 and thence into the metering chamber 4 to fill it.

It can be seen that in the operative orientation of the container and valve as shown, the "U" shaped configuration of the ring 18 around the valve body provides a trough 19 which lies an appreciable distance below the slots 16. The trough serves to accommodate any drug particle sediment that fails to be re-dispersed into suspension, and thus ensures that the suspension entering the sampling chamber 5 through the slots 16 is drawn from a region containing homogenous suspension which is free of drug particle sediment.

The ring 18 further serves to reduce the volume of suspension that can be accommodated within the container below the slots 16. This ensures that most of the contents of the container may be dispensed, the only quantity of suspension that need be wasted corresponding to the reduced volume remaining below the slots after the suspension level has fallen below the level from which it may enter the sampling chamber.

Tables 1 and 2 present end of life actuation weights in mg delivered from two sets of five inhalers each. Both tables show data derived from inhalers containing the equivalent of 160 actuations of a suspension of fluticasone propionate in liquefied HFA134a with a target delivery of 120 actuations plus a 40 actuation overfill to allow for ullage and leakage. Only data from actuation number 115 is shown as the data for both sets of inhalers is consistent up to this point. Table 1 shows data from the first set of five conventional inhalers having valves without a ring. Table 2 shows data from the second set of five inhalers having valves with a ring according to the invention:

TABLE 1

End of Life Actuation weights for valve without ring

| Actuation No. | Actuation weights (mg) | | | | |
| --- | --- | --- | --- | --- | --- |
| | Inhaler 1 | Inhaler 2 | Inhaler 3 | Inhaler 4 | Inhaler 5 |
| 115 | 61 | 60 | 62 | 62 | 61 |
| 116 | 62 | 62 | 62 | 61 | 61 |
| 117 | 61 | 60 | 62 | 61 | 60 |
| 118 | 61 | 61 | 62 | 60 | 60 |
| 119 | 42 | 60 | 62 | 45 | 31 |

TABLE 1-continued

End of Life Actuation weights for valve without ring

| Actuation No. | Actuation weights (mg) | | | | |
| --- | --- | --- | --- | --- | --- |
| | Inhaler 1 | Inhaler 2 | Inhaler 3 | Inhaler 4 | Inhaler 5 |
| 120 | 61 | 61 | 62 | 61 | 62 |
| 121 | 60 | 59 | 61 | 62 | 60 |
| 122 | 60 | 59 | 61 | 61 | 60 |
| 123 | 62 | 61 | 62 | 61 | 61 |
| 124 | 63 | 61 | 62 | 61 | 60 |
| 125 | 62 | 42 | 47 | 47 | 59 |
| 126 | 62 | 59 | 64 | 63 | 60 |
| 127 | 49 | 61 | 53 | 42 | 37 |
| 128 | 61 | 61 | 63 | 61 | 62 |
| 129 | 63 | 57 | 39 | 63 | 63 |
| 130 | 63 | 62 | 63 | 63 | 62 |
| 131 | 60 | 41 | 34 | 38 | 45 |
| 132 | 62 | 61 | 61 | 60 | 59 |
| 133 | 44 | 43 | 39 | 49 | 61 |
| 134 | 60 | 62 | 58 | 62 | 60 |
| 135 | 32 | 60 | 17 | 26 | 44 |
| 136 | 58 | 61 | 60 | 59 | 61 |
| 137 | 49 | 54 | 58 | 51 | 59 |
| 138 | 48 | 45 | 34 | 59 | 59 |
| 139 | 25 | 16 | 14 | 29 | 16 |
| 140 | 37 | 18 | 20 | 5 | 12 |
| 141 | 6 | 8 | 5 | 7 | 18 |
| 142 | 47 | 23 | 30 | 27 | 38 |
| 143 | 10 | 29 | 23 | 15 | 22 |
| 144 | 9 | 16 | 18 | 31 | 36 |
| 145 | 30 | 37 | 29 | 33 | 48 |
| 146 | 42 | 41 | 32 | 30 | 46 |

TABLE 2

End of Life Actuation weights for valve with ring

| Actuation No. | Actuation weights (mg) | | | | |
| --- | --- | --- | --- | --- | --- |
| | Inhaler 1 | Inhaler 2 | Inhaler 3 | Inhaler 4 | Inhaler 5 |
| 115 | 60 | 61 | 61 | 60 | 62 |
| 116 | 62 | 61 | 61 | 61 | 63 |
| 117 | 61 | 60 | 60 | 60 | 61 |
| 118 | 61 | 61 | 61 | 60 | 62 |
| 119 | 60 | 59 | 60 | 60 | 61 |
| 120 | 60 | 61 | 60 | 60 | 62 |
| 121 | 60 | 59 | 60 | 59 | 62 |
| 122 | 60 | 60 | 59 | 59 | 60 |
| 123 | 61 | 61 | 61 | 61 | 61 |
| 124 | 61 | 60 | 61 | 61 | 63 |
| 125 | 61 | 60 | 60 | 59 | 31 |
| 126 | 61 | 60 | 61 | 60 | 62 |
| 127 | 61 | 59 | 61 | 60 | 61 |
| 128 | 61 | 61 | 61 | 60 | 63 |
| 129 | 62 | 58 | 61 | 61 | 57 |
| 130 | 62 | 61 | 61 | 61 | 63 |
| 131 | 60 | 61 | 61 | 60 | 60 |
| 132 | 61 | 60 | 61 | 61 | 62 |
| 133 | 61 | 61 | 61 | 60 | 62 |
| 134 | 61 | 61 | 61 | 61 | 62 |
| 135 | 61 | 60 | 60 | 60 | 62 |
| 136 | 61 | 60 | 60 | 60 | 62 |
| 137 | 59 | 60 | 59 | 58 | 60 |
| 138 | 59 | 59 | 59 | 59 | 60 |
| 139 | 59 | 55 | 59 | 60 | 55 |
| 140 | 31 | 61 | 61 | 59 | 60 |
| 141 | 25 | 48 | 61 | 60 | 33 |
| 142 | 61 | 60 | 61 | 60 | 60 |
| 143 | 21 | 9 | 23 | 20 | 26 |
| 144 | 17 | 25 | 32 | 26 | 25 |
| 145 | 44 | 32 | 36 | 25 | 35 |
| 146 | 17 | 9 | 26 | 19 | 28 |

From Table 1 it can be seen that actuation weight starts to become fairly inconsistent after actuation number 124 for valves without the ring, whereas from Table 2 it can be seen that actuation weight remains fairly consistent up to actuation number 137 and thereafter rapidly tails off for those valves according to the invention incorporating the ring. It is therefore clear that the ring has a significant effect on end of life actuation weight delivered.

Figure 2:
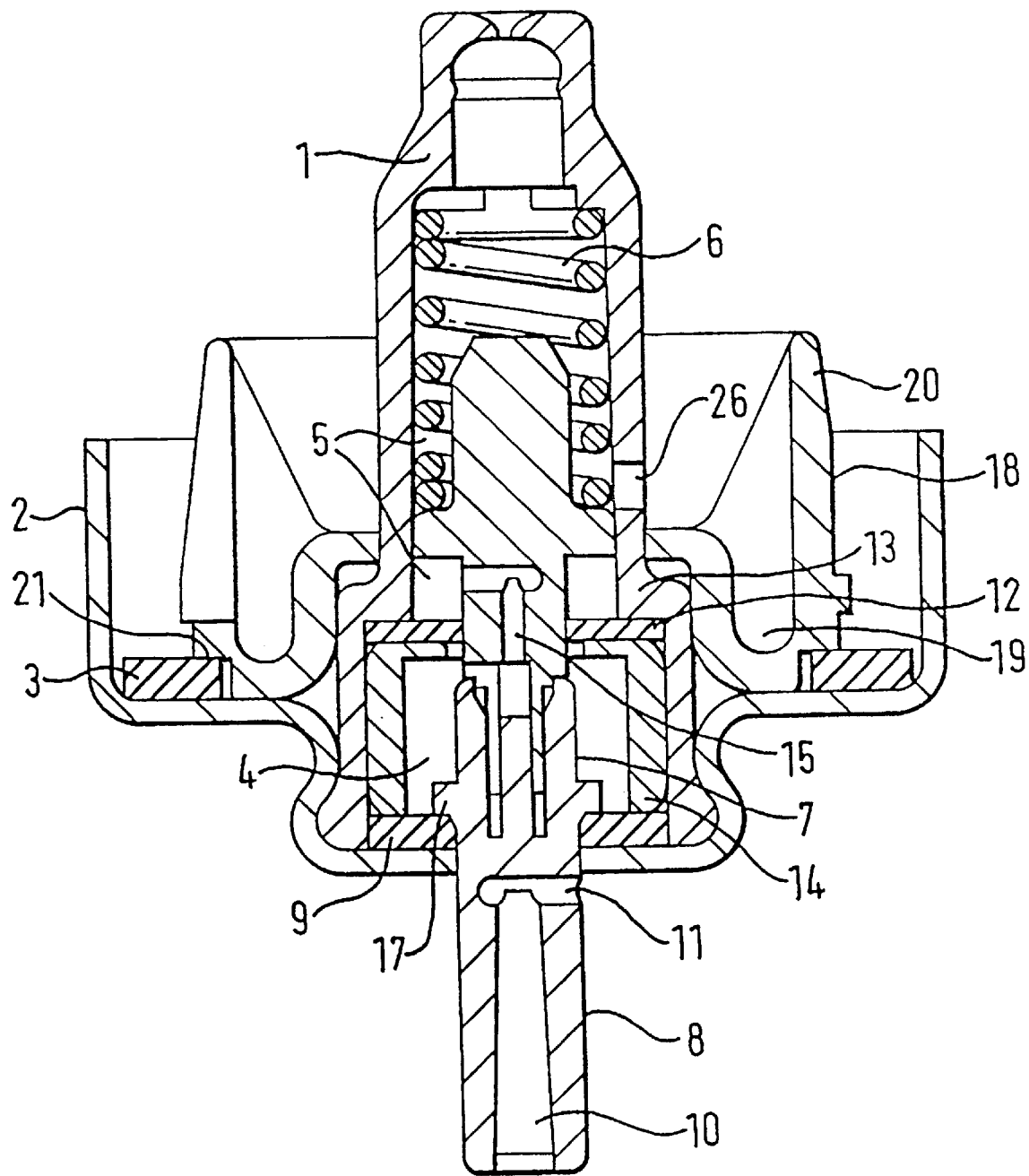
Figure 3:
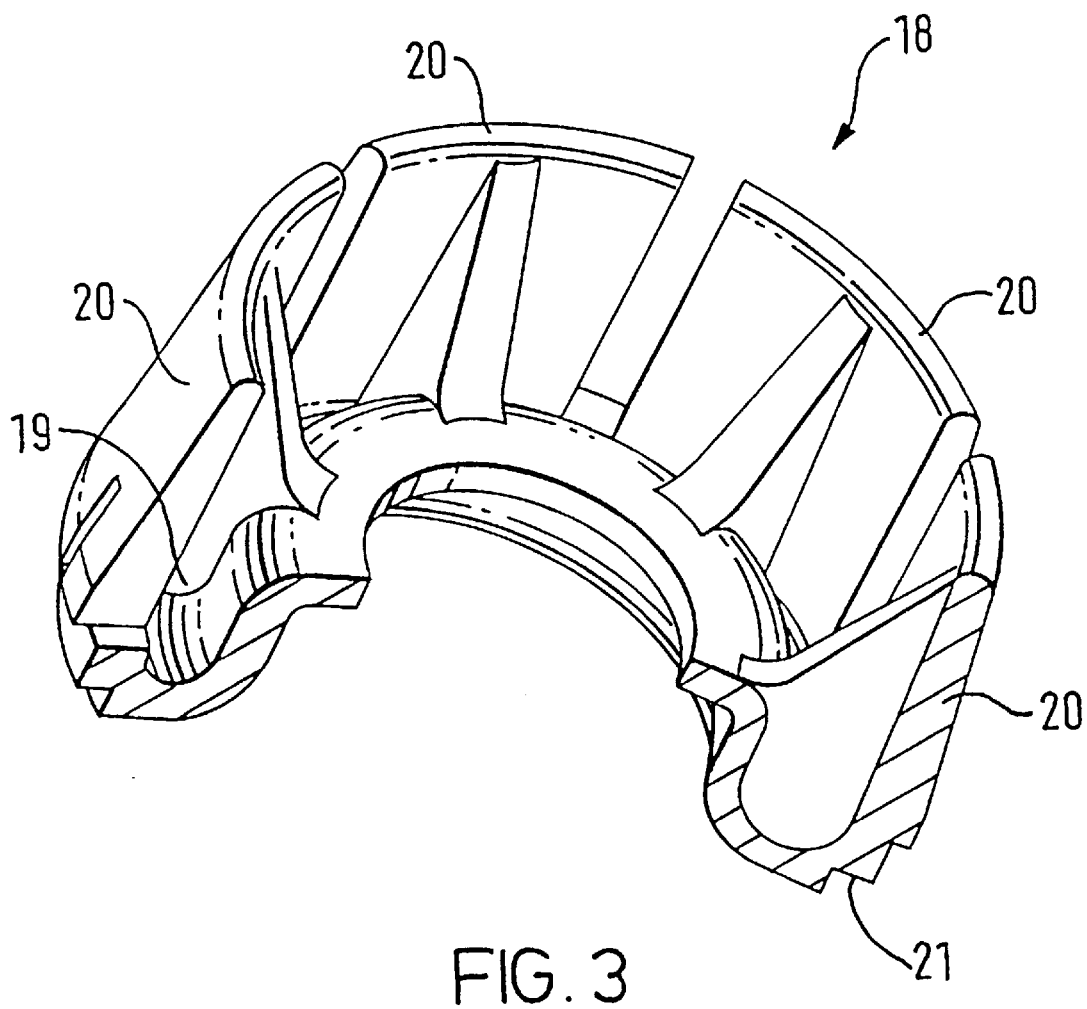

A valve according to a second embodiment of the invention as shown in FIG. 2 is a variant of the valve shown in FIG. 1 in which corresponding elements have been given the same reference numerals as are used in FIG. 1. The main difference between the two embodiments is that the valve of FIG. 2 uses a different design of valve body 1 which has a single orifice 26 allowing communication between sampling chamber 5 and the interior of the container. The valve is operated in exactly the same manner as described with respect to the valve shown in FIG. 1. The valve shown in FIG. 2 might be used with suspensions wherein the problem of sedimentation within the sampling chamber is not so acute but wherein sedimentation around the valve nonetheless remains a problem.

Table 3 demonstrates the improved dose reproducibility achieved using a valve according to the first embodiment of the invention with a body having three slots as shown in FIG. 1 compared to a valve according to the second embodiment of the invention with a body having a single orifice as shown in FIG. 2 when used to dispense a suspension of fluticasone propionate in liquefied HFA134a. The figures given in the table are average dose weights dispensed from at least five inhalers. For each inhaler, doses from two actuations were measured prior to subjecting each inhaler to a vibration test to simulate the effects of transportation, after which doses from two further actuations were measured:

TABLE 3

Effect of vibration on dose delivered

| | Dose ($\mu$g) prior to vibration | | Dose ($\mu$g) after vibration | |
|---|---|---|---|---|
| Valve type | 1st actuation | 2nd actuation | 1st actuation | 2nd actuation |
| Body with single orifice | 233 | 246 | 217 | 688 |
| Body with three slots | 288 | 285 | 275 | 317 |

The data presented in Table 3 clearly shows that the characteristics of extreme dose variability experienced with valves having a single sampling point (orifice), which is due to the highly sedimentary nature of fluticasone propionate in liquefied HFA134a, are considerably reduced with the three slot body.

It will be understood that the present disclosure is for the purpose of illustration only and the invention extends to modifications, variations and improvements thereto.

What is claimed is:

1. A metering valve comprising:
    a valve body;
    a metering chamber;
    a valve stem;
    one or more stem seals;
    at least one orifice in the valve body; and,
    a ring having a trough disposed around the valve body, wherein the ring further includes an annular wall interrupted with a plurality of slots forming a plurality of vanes, wherein, upon shaking of the valve, the suspension flows around the plurality of vanes assisting in dispersion of drug particles in the suspension;
    wherein the metering valve is suitable for dispensing a suspension of drug particles in a liquid propellant, and,
    wherein the drug is a member selected from the group consisting of salmeterol, salbutamol, formoterol, ipratroprium, fluticasone, beclomethasone, budesonide, terbutaline, salts, esters and solvates thereof, and combinations thereof.

2. The metering valve of claim 1 including an upper stem seal and a lower stem seal.

3. The metering valve of claim 2, wherein the ring further includes a seat adapted to accommodate a gasket to seal the container.

4. The metering valve of claim 1, wherein the at least one orifice is at least one slot extending substantially axially.

5. The metering valve of claim 1 further including a sampling chamber, wherein the at least one slot extends substantially the axial length of the sampling chamber.

6. The metering valve of claim 5 including more than two slots.

7. The valve of claim 1 including more than 2 slots and more than 2 vanes.

8. The valve of claim 1 wherein the drug is fluticasone propionate.

9. The metering valve of claim 1, wherein the ring is further capable of reducing the volume of suspension accompanied within a container below the at least one orifice when the container is oriented with the valve at the bottom, wherein the trough is circumferential around the valve body.

10. The metering valve of claim 1 comprising 6 slots and 6 vanes.

11. The metering valve of claim 1 wherein the drug is a combination of a salt, ester or solvate of salmeterol and fluticasone.

12. The metering valve of claim 11, wherein the drug is a combination of salmeterol xinafoate and fluticasone propionate.

13. The metering valve of claim 1, wherein the drug is salmeterol xinafoate.

14. The metering valve of claim 1, wherein the drug is salbutamol sulfate.

15. The metering valve of claim 1, wherein the drug is beclomethasone dipropionate.

16. The metering valve of claim 1, wherein the drug is a combination of ipratroprium bromide and salmeterol xinafoate.

17. The metering valve of claim 1, wherein the ring is constructed from nylon.

18. The metering valve of claim 1, wherein the ring is adapted to be friction fitted with the valve body.

19. The metering valve of claim 18, wherein the ring includes an inner annular contacting rim adapted to friction fitted to the valve body.

20. The metering valve of claim 1, wherein the propellant is HFA 134A.

21. A metering valve comprising:
    a valve body;
    a means for metering a suspension of drug particles in a liquid propellant;
    a valve stem;
    one or more means for sealing the valve stem;
    at least one orifice in the valve body;
    a ring disposed around the valve body and positioned below the at least one orifice;
    a means, below the at least one orifice, for collecting drug particle sediment; and, means for assisting in the dispersion of the drug particles in the liquid propellant, wherein the metering valve is suitable for dispensing the suspension, and wherein the drug is a member selected from the group consisting of salmeterol salbutamol, formoterol, ipratroprium, fluticasone, beclomethasone, budesonide, terbutaline, salts, esters and solvates thereof, and combinations thereof.

22. A metering valve comprising:

a valve body;

at least one orifice, a sampling chamber having an axial length, a ring having a trough and an annular wall interrupted with a plurality of slots and a plurality of vanes, the ring disposed around the valve body, a metering chamber, a transfer passage between the sampling chamber and the metering chamber, a valve stem, one or more stem seals; and, a dispensing passage within the valve stem, wherein the valve stem is slibeably moveable within the valve body such that in a first position the dispensing passage is isolated from the metering chamber and the metering chamber is in communication with the sampling chamber via the transfer passage, wherein the valve stem is slideably moveable within the valve body such that in a second position the dispensing passage is in communication with the metering chamber and the transfer passage is isolated from the metering chamber, wherein the metering valve is suitable for dispensing a suspension of drug particles in a liquid propellant, and wherein the drug is a member selected from the group consisting of salmeterol, salbutamol, formoterol, ipratroprium, fluticasone, beclomethasone, budesonide, terbutaline, salts, esters and solvates thereof, and combinations thereof.

23. A metered dose inhaler comprising:

an aerosol container containing a suspension of drug particles in a liquid propellant in communication with a valve comprising:

a valve body;
a metering chamber;
a valve stem;
one or more stem seals;
at least one orifice in the valve body to allow a quantity of the suspension to pass from the container into the valve; and,
a ring having a trough disposed around the valve body, wherein the ring further includes an annular wall interrupted with a plurality of slots forming a plurality of vanes, wherein, upon shaking of the aerosol container, the suspension flows around the plurality of vanes assisting in dispersion of drug particles in the suspension, and,
wherein the drug is a member selected from the group consisting of salmeterol, salbutamol, formoterol, ipratroprium, fluticasone, beclomethasone, budesonide, terbutaline, salts, esters and solvates thereof, and combinations thereof.

24. The metered dose inhaler of claim 23 wherein the drug is salmeterol xinafoate.

25. The metered dose inhaler of claim 23 wherein the drug is salbutamol sulphate.

26. The metered dose inhaler of claim 23 wherein the drug is beclomethasone dipropionate.

27. The metered dose inhaler of claim 23 wherein the drug is a combination of salmeterol xinafoate and fluticasone propionate.

28. The metered dose inhaler of claim 23 wherein the drug is a combination of a salt, ester or solvate of salmeterol and ipratroprium.

29. The metered dose inhaler of claim 28 wherein the drug is a combination of salmeterol xinafoate and ipratroprium bromide.

30. The metered dose inhaler of claim 23 wherein the propellant is 1,1,1,2-tetrafluoroethane.

31. The metered dose inhaler of claim 23, wherein the at least one orifice is at least one slot extending substantially axially.

32. The metered dose inhaler of claim 23 further including a sampling chamber, wherein the at least one slot extends substantially the axial length of the sampling chamber.

33. The metered dose inhaler of claim 23 including more than two slots.

34. The metered dose inhaler of claim 23, wherein the ring further includes a seat adapted to accommodate a gasket to seal the container.

35. The metered dose inhaler of claim 23 including more than 2 slots and more than 2 vanes.

36. The metered dose inhaler of claim 23 wherein the ring is further capable of reducing the volume of suspension accompanied within the container below the at least one orifice when the container is oriented with the valve at the bottom, wherein the trough is circumferential around the valve body, and wherein the trough is provided by a portion of reduced axial thickness in the ring below the at least one orifice.

37. The metered dose inhaler of claim 23 wherein the drug is a member selected from the group consisting of formoterol, terbutaline, and salts, esters and solvates thereof.

38. The metered dose inhaler of claim 23 comprising 6 slots and 6 vanes.

39. A metered dose inhaler comprising:

a means for containing a suspension of drug particles in a liquid propellant in communication with a valve comprising:

a valve body;
a means for metering the suspension;
a valve stem;
one or more means for sealing the valve stem;
at least one orifice in the valve body to allow a quantity of the suspension to pass from the containing means into the valve; and,
a ring having a means, disposed around the valve body, for collecting drug particle sediment,
wherein the ring further includes an annular wall interrupted with a plurality of slots forming a plurality of vanes, wherein, upon shaking of the containing means, the suspension flows around the plurality of vanes assisting in dispersion of drug particles in the suspension, and,
wherein the drug is a member selected from the group consisting of salmeterol, salbutamol, formoterol, ipratroprium, fluticasone, beclomethasone, budesonide, terbutaline, salts, esters and solvates thereof, and combinations thereof.

* * * * *